United States Patent
Treuner et al.

[11] 3,946,001
[45] Mar. 23, 1976

[54] (CARBAMOYLTHIOACETYL)CEPHALOSPORIN DERIVATIVES

[75] Inventors: Uwe D. Treuner; Hermann Breuer, both of Regensburg, Germany

[73] Assignee: E. R. Squibb & Sons, Inc., Princeton, N.J.

[22] Filed: May 17, 1974

[21] Appl. No.: 471,080

[52] U.S. Cl..... 260/243 C; 260/455 A; 260/326.44; 424/246
[51] Int. Cl.$^2$......................... C07D 501/32
[58] Field of Search ................................ 260/243 C

[56] References Cited
UNITED STATES PATENTS
3,391,141 7/1968 Gottstein et al. ............... 260/243 C FOREIGN PATENTS OR APPLICATIONS
2,241,250 3/1973 Germany.................. 260/243 C
2,253,800 5/1973 Germany.................. 260/243 C
49-00296 1/1974 Japan OTHER PUBLICATIONS
Gottstein et al., J. Med. Chem. Vol. 14, No. 8, pp. 770–772 (1971).

Primary Examiner—Alton D. Rollins
Assistant Examiner—Diana G. Rivers
Attorney, Agent, or Firm—Lawrence S. Levinson; Merle J. Smith

[57] ABSTRACT

(Carbamoylthioacetyl)cephalosporin derivatives of the general formula

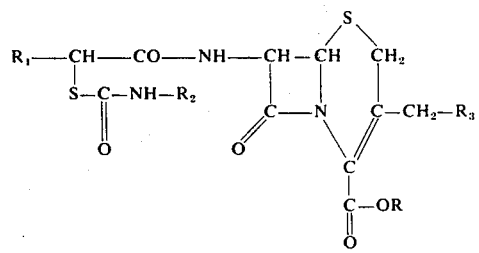

wherein R is hydrogen, lower alkyl, phenyl-lower alkyl, tri(lower alkyl)stannyl, tri(lower alkyl)silyl, a salt forming ion or the group

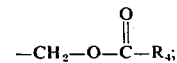

$R_1$ is hydrogen, lower alkyl, phenyl, thienyl or furyl; $R_2$ is lower alkyl, lower alkoxymethyl, phenyl or phenyl-lower alkyl; $R_3$ is hydrogen, hydroxy or lower alkanoyloxy; and $R_4$ is lower alkyl, phenyl or phenyl-lower alkyl; are useful as antibacterial agents.

12 Claims, No Drawings

(CARBAMOYLTHIOACETYL)CEPHALOSPORIN DERIVATIVES

SUMMARY OF THE INVENTION

This invention relates to new (carbamoylthioacetyl) cephalosporin derivatives of the formula

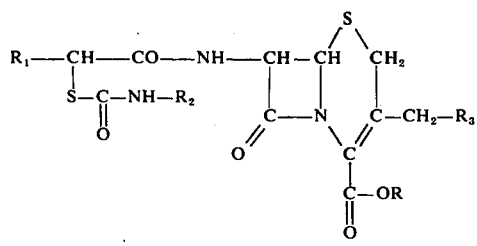

R represents hydrogen, lower alkyl, phenyl-lower alkyl, tri(lower alkyl)stannyl, tri(lower alkyl)silyl, a salt forming ion or the group

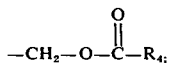

$R_1$ represents hydrogen, lower alkyl, phenyl, thienyl or furyl; $R_2$ represents lower alkyl, lower alkoxymethyl, phenyl or phenyl-lower alkyl; $R_3$ represents hydrogen, hydroxy or lower alkanoyloxy; and $R_4$ represents lower alkyl, phenyl or phenyl-lower alkyl.

The preferred members within each group are as follows: R is hydrogen, alkali metal, trimethylsilyl, benzhydryl, or

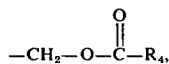

especially hydrogen, pivaloyloxymethyl, sodium or potassium; $R_1$ is hydrogen, lower alkyl or phenyl, especially hydrogen or phenyl; $R_2$ is lower alkyl, especially methyl or ethyl, or lower alkoxymethyl, especially methoxymethyl; $R_3$ is preferably hydrogen or acetoxy; and $R_4$ is methyl or t-butyl.

DETAILED DESCRIPTION OF THE INVENTION

The various groups represented by the symbols have the meanings defined below and these definitions are retained throughout this specification.

The lower alkyl groups are the straight and branched chain hydrocarbon groups in the series from methyl to heptyl, the $C_1$ to $C_4$ members and especially methyl and ethyl being preferred.

The lower alkanoyloxy groups represented by $R_3$ include the acyl radicals of lower fatty acids containing alkyl radicals of the type described above, e.g., acetoxy, propionoxy, butyryloxy, etc., acetoxy being preferred.

The phenyl-lower alkyl radicals include a phenyl ring attached to a lower alkyl group of the kind described above as well as those containing two phenyl groups such as benzhydryl.

The salt forming ions represented by R are metal ions, e.g., alkali metal ions such as sodium or potassium, alkaline earth metal ions such as calcium or magnesium, or an amine salt ion, e.g., a (lower alkyl)amine like methylamine or triethylamine, etc.

The new (carbamoylthioacetyl)cephalosporin derivatives of this invention are produced by reacting a 7-aminocephalosporanic acid compound [which includes 7-aminocephalosporanic acid (7-ACA), 7-amino-3-desacetoxycephalosporanic acid (7-ADCA) and other derivatives] of the formula

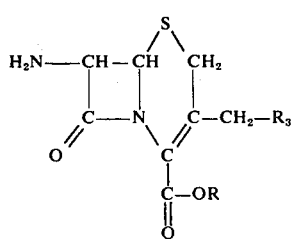

with a carbamoylacetic acid of the formula

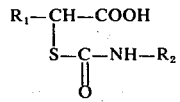

or an activated derivative of the former (II).

The activated derivatives referred to include, for example, the reaction product with an anhydride forming reagent such as ethylchloroformate, benzoyl chloride, pivaloyl chloride, etc., or an activated ester like the benzhydryl ester, t-butyl ester, trimethylsilyl ester or trimethylstannyl ester or triethylamine salt. Dicyclohexylcarbodiimide can also be used to effect the reaction.

One preferred synthesis comprises reacting the acid of formula III with the benzhydryl ester of 7-ACA or 7-ADCA and then hydrolyzing the ester with trifluoroacetic acid and anisole to obtain the free carboxyl group in the 4-position.

Another preferred synthesis comprises forming the 2,5-dioxo-1-pyrrolidinyl ester by reacting the acid of formula III with N-hydroxysuccinimide in the presence of dicyclohexylcarbodiimide, reacting the product with the benzhydryl ester of 7-ACA or 7-ADCA and hydrolyzing the product of that reaction with trifluoroacetic acid and anisole.

The reaction between the 7-aminocephalosporanic acid compound and the carbamoylacetic acid can be carried out, for example, by dissolving or suspending the acid in an inert organic solvent such as chloroform, tetrahydrofuran, methylene chloride, dioxane, benzene or the like, and adding, at a reduced temperature of about 0°–5°C, about an equimolar amount of the 7-ACA or 7-ADCA compound in the presence of an activating compound such as dicyclohexylcarbodiimide. The product of the reaction is then isolated by conventional procedures, e.g., by concentration or evaporation of the solvent. If a derivativve of the 7-aminocephalosporanic acid compound, such as the benzhydryl ester is used, the free acid is obtained by hydrolysis, e.g., with trifluoroacetic acid or the like. Salts can then be derived from the free acid.

When R is the acyloxymethyl group

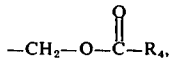

this group can be introduced into the 7-aminocephalosporanic acid moiety prior to the reaction with the carbamoylthioacetic acid or the activated derivative by treatment with one to two moles of a halomethyl ester of the formula (IV)

wherein hal is halogen, preferably chlorine or bromine, in an inert organic solvent such as dimethylformamide, acetone, dioxane, benzene or the like, at about ambient temperature or below.

The carbamoylacetic acid of formula III is produced by reacting a mercaptoacetic acid of the formula

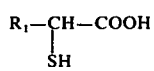 (V)

with a base, e.g., an alkylamine like triethylamine, and with an isocyanate $R_2N=C=O$, in an inert solvent like tetrahydrofuran, then acidifying, e.g., with hydrochloric acid or the like.

Alternatively the acid of formula V is converted to an ester like the benzhydryl ester by reaction with a diazomethane like diphenyldiazomethane, followed by reaction with the isocyanate and treatment with trifluoroacetic acid/anisole.

Further process details are also provided in the illustrative examples.

Certain of the compounds of this invention may exist in different optically active forms. The various stereoisomeric forms as well as the racemic mixtures are within the scope of the invention.

The compounds of this invention have a broad spectrum of antibacterial activity against both gram positive and gram negative organisms such as *Staphylococcus aureus*, *Salmonella schottmuelleri*, *Pseudomonas aeruginosa*, *Proteus vulgaris*, *Escherichia coli* and *Streptococcus pyogenes*. They are useful as antibacterial agents, e.g., to combat infections due to organisms such as those named above, and in general they can be utilized in a manner similar to cephradine and other cephalosporins. For example, a compound of formula I or a physiologically acceptable salt thereof can be used in various animal species affected by infections of such bacterial origin in an amount of about 1 to 75 mg/kg daily, orally or parenterally, in single or two to four divided doses.

Up to about 600 mg. of a compound of formula I or a physiologically acceptable salt thereof is administered by incorporating in an oral dosage form such as tablets, capsules or elixirs or in an injectable form in a sterile aqueous vehicle prepared according to conventional pharmaceutical practice.

The following examples are illustrative of the invention. All temperatures are in degrees celsius. Additional variations are produced in the same manner by appropriate substitution in the starting material.

EXAMPLE 1

DL-[(Methylcarbamoyl)thio]phenylacetic acid 10.08 g. (60 mM) of α-mercaptophenylacetic acid and 6.6 g. (60 mM) of triethylamine are dissolved in 50 ml. of tetrahydrofuran and 3.42 g. (60 mM) of methylisocyanate dissolved in 20 ml. of tetrahydrofuran are added dropwise with stirring. After stirring for 2 hours, the solvent is drawn off in a vacuum and the oily residue is dissolved in water. The mixture is then acidified with 2N hydrochloric acid and extracted three times each with 20 ml. of ether. After drying off the ether, 10.5 g. of white crystalline DL-[(methylcarbamoyl)thio]phenylacetic acid are obtained, which is recrystallized from ether/petroleum ether, m.p. 128°–129°.

EXAMPLE 2

DL-[(Ethylcarbamoyl)thio]phenylacetic acid

By substituting ethylisocyanate for the methylisocyanate in the procedure of Example 1, white crystalline DL-[(ethylcarbamoyl)thio]phenylacetic acid is obtained and recrystallized from cyclohexane, m.p. 115°–117° (dec.).

EXAMPLE 3

DL-α-[[[(Methoxymethyl)amino]carbonyl]thio]-phenylacetic acid

By substituting methoxymethyl isocyanate for the methylisocyanate in the procedure of Example 1, white crystalline DL-α-[[[(methoxymethyl)amino]carbonyl]thio]phenylacetic acid is obtained and recrystallized from cyclohexane, m.p. 111°–112°.

EXAMPLE 4

DL-3-[(Acetyloxy)methyl]-7β-[[[[(methylamino)carbonyl]thio]phenylacetyl]amino]-8-oxo-5-thia-1-azabicyclo[4.2.0]oct-2-ene-carboxylic acid, diphenylmethyl ester 1 g. (5 mM) of dicyclohexylcarbodiimide is added to 1.1 g. (5 mM) of DL-[(methylcarbamoyl)thio]phenyl acetic acid in 50 ml. of tetrahydrofuran and stirred for 1 hour at −5°. 2.1 g. (5 mM) of 7-aminocephalosporanic acid, benzhydryl ester in 15 ml. of tetrahydrofuran are then added and the mixture is stirred for 5 hours at 0° and for 1 hour at room temperature. The precipitate of dicyclohexylurea is filtered off and the filtrate is evaporated. The oily residue is dissolved in 20 ml. of methylene chloride. Filtration over charcoal and precipitation with petroleum ether produces 1.3 g. of white DL-3-[(acetyloxy)methyl-7β-[[[[(methylamino)-carbonyl]thio]phenyl]acetyl]amino]-8-oxo-5-thia-1-azabicyclo-[4.2.0]oct-2-ene-carboxylic acid, diphenylmethyl ester which is reprecipitated from methylene chloride/carbon tetrachloride, m.p. 73° (dec.).

EXAMPLE 5

DL-3-[(Acetyloxy)methyl]-7β-[[[[(methylamino)carbonyl]thio]-phenylacetyl]amino]-8-oxo-5-thia-1-azabicyclo[4.2.0]oct-2-ene-carboxylic acid 3 g. of the product of Example 4 are dissolved at 0° in 25 ml. of trifluoroacetic acid/anisole and stirred for 15 minutes. After drawing off the trifluoroacetic acid in vacuum, an oily residue remains which is washed repeatedly with absolute ether until it becomes quite firm. The residue is dissolved in sodium bicarbonate solution, filtered and acidified with hydrochloric acid, with cooling, to a pH of 2.5. The solution is extracted three times each with 20 ml. of ethyl acetate. The organic phase is dried and evaporated. 0.9 g. of DL-3-

[(Acetyloxy)methyl]-7β-[[[[(methylamino)carbonyl]thio]phenylacetyl]-amino]-8-oxo-5-thia-1-azabicyclo[4.2.0]oct-2-ene-carboxylic acid is obtained as a light yellow powder m.p. 121° (dec.) after reprecipitation from methylene chloride/petroleum ether.

EXAMPLE 6

DL-3-[(Acetyloxy)methyl]-7β-[[[[(methylamino)carbonyl]thio]-phenylacetyl]amino]-8-oxo-5-thia-1-azabicyclo[4.2.0]oct-2-ene-2-carboxylic acid, potassium salt dihydrate By freeze drying a molecular equivalent aqueous solution of the product of Example 5 in potassium bicarbonate, DL-3-[(acetyloxy)methyl]-7β-[[[[(methylamino)carbonyl]thio]-phenylacetyl]amino]-8-oxo-5-thia-1-azabicyclo[4.2.0]oct-2-ene-2-carboxylic acid, potassium salt dihydrate is obtained as a beige powder, m.p. 152°.

EXAMPLE 7

Alternate method for producing the product of Example 5

4.5 g. (20 mM) of DL-[(methylcarbamoyl)thio]-phenylacetic acid are dissolved in 50 ml. of tetrahydrofuran. 2 g. (20 mM) of triethylamine are added and while stirring at a temperature of 0° 2.5 g. (20 mM) of ethyl chloroformate are added dropwise. After one hour, a solution of 5.4 g. (20 mM) of 7-aminocephalosporanic acid, triethylamine salt in 200 ml. of methylene chloride are added and the whole mixture is stirred for 14 hours at 5°. After filtering and drawing off the solvent, the oily residue is treated with water. The aqueous solution is extracted with ethyl acetate, filtered and acidified to pH 2.5. Repeated extraction with ethyl acetate and evaporation of the ethyl acetate solution in vacuum yields after recrystallization from methylene chloride/petroleum ether, DL-3-[(acetyloxy)methyl]-7β-[[[[(methylamino)-carbonyl]thio]phenylacetyl]amino]-8-oxo-5-thia-1-azabicyclo[4.2.0]oct-2-ene-carboxylic acid as a light yellow powder, 2.5 g., m.p. 61°. The product produced by this method is only 67% pure.

EXAMPLE 8

3-[(Acetyloxy)methyl]-7β-[[[[(methoxymethyl)amino]carbonyl]-thio]phenylacetyl]amino]-8-oxo-5-thia-1-azabicyclo[4.2.0]oct-2-ene-2-carboxylic acid, diphenylmethyl ester The procedure of Example 4 is followed using 4.2 g. (10 mM) 7-ACA-benzhydryl ester, 2.5 g. (10 mM) of DL-α-[[[(methoxymethyl)amino]carbonylthio]-phenylacetic] acid and 2.06 g. (10 mM) of dicyclohexylcarbodiimide in 50 ml. of tetrahydrofuran. After reprecipitation from methylene chloride/petroleum ether, 3.8 g. of 3-[(acetyloxy)methyl]-7β-[[[[(methoxymethyl)amino]carbonyl]thio]phenylacetyl]amino]-8-oxo-5-thia-1-azabicyclo[4.2.0]oct-2-ene-2-carboxylic acid, diphenylmethyl ester are obtained as a cream-colored powder, m.p. 93°.

EXAMPLE 9

DL-3-[(Acetyloxy)methyl]-7β-[[[[(methoxymethyl)amino]carbonyl]-thio]phenyacetyl]amino]-8-oxo-5-thia-1-azabicyclo[4.2.0]oct-2-ene-2-carboxylic acid After treating the ester of Example 8 with trifluoroacetic acid/anisole DL-3-[(acetyloxy)methyl]-7β-[[[[(methoxymethyl)-amino]carbonyl]thio]-phenylacetyl]amino]-8-oxo-5-thia-1-azabicyclo[4.2.-0]oct-2-ene-2-carboxylic acid is obtained in the form of a beige powder, m.p. 121° after reprecipitation from methylene chloride/carbon tetrachloride.

EXAMPLE 10

DL-3-[(Acetyloxy)methyl]-7β-[[[[(methoxymethyl)amino]carbonyl]-thio]phenylacetyl]amino]-8-oxo-5-thia-1-azabicyclo[4.2.0]oct-2-ene-2-carboxylic acid, potassium salt By the freeze drying a molecular equivalent solution of the product of Example 9 in aqueous potassium bicarbonate, DL-3-[(acetyloxy)methyl]-7β-[[[[(methoxymethyl)amino]carbonyl]-thio]phenylacetyl-]amino]-8-oxo-5-thia-1-azabicyclo[4.2.0]oct-2-ene-2-carboxylic acid, potassium salt is obtained as a beige powder, m.p. 146°.

EXAMPLE 11

DL-3-[(Acetyloxy)methyl]-7β-[[[[(ethylamino)carbonyl]thio]-phenylacetyl]amino]-8-oxo-5-thia-1-azabicyclo[4.2.0]oct-2-ene-2-carboxylic acid, diphenylmethyl ester 4.8 g. (20 mM) of DL-[(ethylcarbamoyl)thio]-phenylacetic acid are dissolved in 150 ml. of tetrahydrofuran and stirred with 8.4 g. (20 mM) of 7-ACA benzhydryl ester and 4.05 g. (20 mM) of dicyclohexylcarbodiimide for 8 hours at 0°. By evaporating the filtered solution, 9 g. of DL-3-[(acetyloxy)methyl]-7β-[[[[(ethylamino)carbonyl]thio]phenylacetyl]amino]-8-oxo-5-thia-1-azabicyclo[4.2.0]oct-2-ene-2-carboxylic acid, diphenylmethyl ester are obtained as a yellow powder, m.p. 75° (dec.).

EXAMPLE 12

α-[[(Methylamino)carbonyl]thio]phenylacetic acid, 2,5-dioxo-1-pyrrolidinyl ester 4.5 g. (20 mM) of DL-[(methylcarbamoyl)thio]-phenylacetic acid are stirred with 2.3 g. (20 mM) of N-hydroxysuccinimide and 4.05 g. (20 mM) of dicyclohexylcarbodiimide in 150 ml. of tetrahydrofuran at 0° for 18 hours. Evaporation of the filtered solution and recrystallization from benzene yields 5.6 g. of α-[[(methylamino)carbonyl]thio]phenylacetic acid, 2,5-dioxo-1-pyrrolidinyl ester as light yellow crystals, m.p. 153°–156°.

The following additional products having the formula (c) in the table are obtained by the procedure of Example 4 by substituting for the 7-aminocephalosporanic acid benzhydryl ester, the starting material (a), and for the [(methylcarbamoyl)thio]phenylacetic acid, the starting material (b) with the substituents indicated in the table:

TABLE

 (a)    (b)    (c)

| Example | R | $R_1$ | $R_2$ | $R_3$ |
|---|---|---|---|---|
| 13 | $-CH_3$ | H | $-CH_3$ | H |
| 14 | $-C_2H_5$ | $-CH_3$ | $-C_2H_5$ | $-OH$ |
| 15 | $-CH(C_6H_5)_2$ | $-C_3H_7$ | $-C_2H_5$ | $-OCOCH_3$ |
| 16 | $-CH_2OC(=O)-CH(CH_3)_2$ | $-CH_2OCH_3$ | $-CH_3$ | $-OCOCH_3$ |
| 17 | $-CH_2OC(=O)-C_6H_5$ | $C_6H_5$ | $-CH_3$ | $-OCOCH_3$ |
| 18 | $-C_2H_4-C_6H_5$ | $C_6H_5-$ | $-C_2H_5$ | H |
| 19 | H | 2-thienyl | $-C_2H_5$ | $-OCOCH_3$ |
| 20 | $-Sn(CH_3)_3$ | 2-thienyl | $-CH_3$ | $-OH$ |
| 21 | $-CH(C_6H_5)_2$ | 2-thienyl | $-CH_3$ | $-OCOCH_3$ |
| 22 | $Si(CH_3)_3$ | $C_6H_5$ | n-butyl | $-OH$ |
| 23 | H | $C_6H_5$ | $C_3H_7$ | $-OCOCH_3$ |
| 24 | Na | 2-thienyl | $-C_2H_5$ | H |
| 25 | K | 2-furyl | $-CH_3$ | $-OCOCH_3$ |
| 26 | H | H | $-C_2H_5$ | $-OCOCH_3$ |
| 27 | $-CH(C_6H_5)_2$ | H | $-CH_2OC_2H_5$ | $-OCOCH_3$ |
| 28 | H | $C_6H_5-$ | $-CH_2OCH_3$ | H |
| 29 | H | $C_6H_5-$ | $C_6H_5-$ | $-OCOCH_3$ |
| 30 | H | $C_6H_5-$ | $-CH_2C_6H_5$ | H |

TABLE-continued

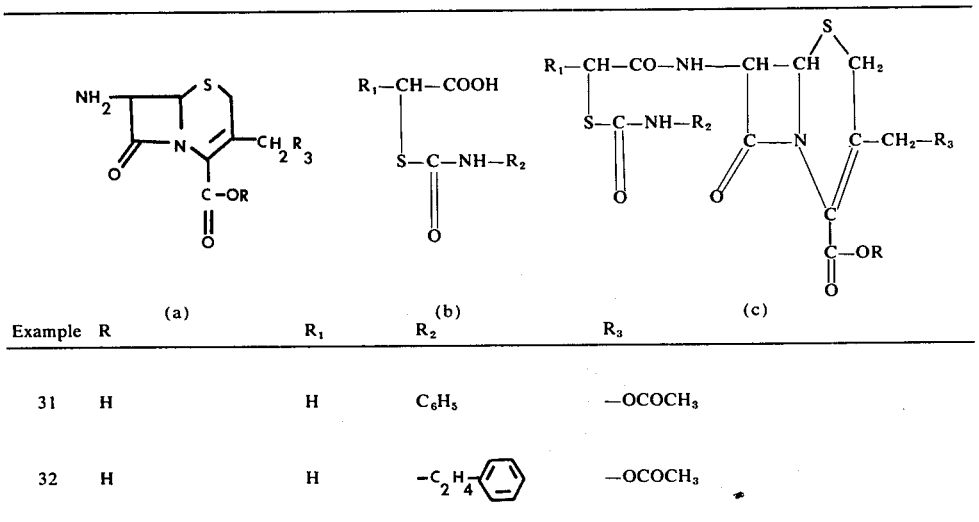

| Example | (a) R | R₁ | (b) R₂ | (c) R₃ |
|---|---|---|---|---|
| 31 | H | H | C₆H₅ | —OCOCH₃ |
| 32 | H | H | —C₂H₄—⟨phenyl⟩ | —OCOCH₃ |

What is claimed is:

1. A compound of the formula

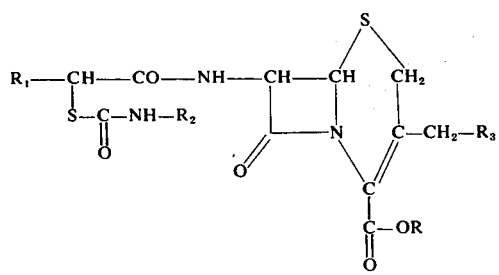

wherein R is hydrogen, lower alkyl, phenyl-lower alkyl, diphenyl-lower alkyl, tri(lower alkyl)stannyl, tri(lower alkyl)silyl,

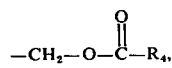

alkali metal, alkaline earth metal, tri-lower alkylamine salt or (lower alkyl)amine salt; $R_1$ is phenyl; $R_2$ is lower alkyl, lower alkoxymethyl, phenyl or phenyl-lower alkyl; $R_3$ is hydrogen, hydroxy or lower alkanoyloxy; and $R_4$ is lower alkyl, phenyl or phenyl-lower alkyl; said lower alkyl and lower alkanoyloxy groups having up to seven carbon atoms.

2. A compound as in claim 1 wherein $R_2$ is lower alkyl.

3. A compound as in claim 1 wherein R is hydrogen and $R_2$ is lower alkyl.

4. A compound as in claim 1 wherein R is hydrogen, $R_1$ is phenyl, $R_2$ is lower alkyl and $R_3$ is lower alkanoyloxy.

5. A compound as in claim 1 wherein R is alkali metal, $R_1$ is phenyl, $R_2$ is lower alkyl and $R_3$ is lower alkanoyloxy.

6. A compound as in claim 1 wherein R is hydrogen, $R_1$ is phenyl, $R_2$ is lower alkoxymethyl and $R_3$ is hydrogen.

7. A compound as in claim 4 wherein the lower alkyl group is methyl and the lower alkanoyloxy group is acetoxy.

8. Alkali metal salt of the compound of claim 7.

9. A compound as in claim 4 wherein the lower alkyl group is ethyl and the lower alkanoyloxy group is acetoxy.

10. A compound as in claim 1 wherein R is hydrogen, $R_1$ is phenyl, $R_2$ is lower alkoxymethyl and $R_3$ is lower alkanoyloxy.

11. A compound as in claim 10 wherein $R_2$ is methoxymethyl and $R_3$ is acetoxy.

12. A compound of the formula

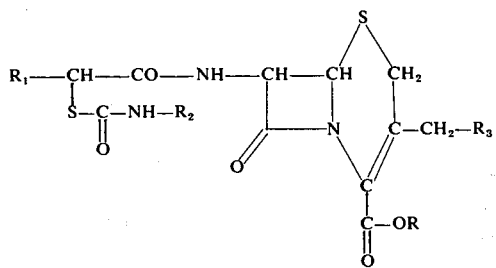

wherein R is hydrogen, lower alkyl, phenyl-lower alkyl, diphenyl-lower alkyl, tri(lower alkyl)stannyl, tri(lower alkyl)silyl,

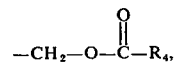

alkali metal, alkaline earth metal, tri(lower alkyl)amine salt or (lower alkyl)amine salt; $R_1$ is thienyl; $R_2$ is lower alkyl, lower alkoxymethyl, phenyl or phenyl-lower alkyl; $R_3$ is hydrogen, hydroxy or lower alkanoyloxy; and $R_4$ is lower alkyl, phenyl or phenyl-lower alkyl; said lower alkyl and lower alkanoyloxy groups having up to seven carbon atoms.

* * * * *